US00PP16992P2

(12) United States Plant Patent
Danziger

(10) Patent No.: US PP16,992 P2
(45) Date of Patent: Aug. 15, 2006

(54) *SUTERA* PLANT NAMED 'DANCOPINK'

(50) Latin Name: ***Sutera* sp.**
Varietal Denomination: Dancopink

(75) Inventor: Gabriel Danziger, Moshav Nir-Zvi (IL)

(73) Assignee: Danziger "Dan" FLower Farm, Post Beit Dagan (IL)

( * ) Notice: Subject to any disclaimer, the term of this patent is extended or adjusted under 35 U.S.C. 154(b) by 0 days.

(21) Appl. No.: 11/068,872

(22) Filed: Mar. 2, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
*Assistant Examiner*—Georgia Helmer
(74) *Attorney, Agent, or Firm*—Foley & Lardner LLP

(57) ABSTRACT

A new and distinct *Sutera* plant named 'Dancopink' particularly characterized by having 5-petalled violet-colored flowers with a yellow throat measuring 1.5 cm in diameter; trailing vigorous growth; early flowering response; and suitable for use with hanging basket planters, combination planters and ground cover under full sunlight- and slight shade.

2 Drawing Sheets

Botanical designation: *Sutera* sp.
Variety denomination: 'Dancopink'.

BACKGROUND OF THE INVENTION

The present invention relates to a new and distinct cultivar of *Sutera* plant, botanically known as *Sutera* sp., hereinafter referred to by the cultivar name 'Dancopink'.

*Sutera,* of the Scrophulriaceae family, consists of annuals which are grown in most climate zones in the U.S., and only in zones 9 and 10 if it is a perennial plant.

The new *Sutera* cultivar is a product of a planned breeding program conducted by the inventor, Gabriel Danziger, in Moshav Mishmar Hashiva, Israel. The objective of the breeding program was to develop a new *Sutera* variety with large, pink flowers and branched, compact growth habit.

The new *Sutera* cultivar originated from a cross made in a controlled breeding program by the inventor in 2003, in Moshav Mishmar Hashiva, Israel. The female parent is a proprietary cultivar designated 'CV-03-53' (unpatented). The male parent is open pollination. The new *Sutera* cultivar 'Dancopink' was discovered and selected by the inventor, Gabriel Danziger, as a flowering plant within the progeny of the stated cross in a controlled environment in Moshav Mishmar Hashiva, Israel.

Asexual reproduction of the new *Sutera* cultivar by vegetative cutting was first performed in July, 2003 in Moshav Mishmar Hashiva, Israel, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'Dancopink' which in combination distinguish this *Sutera* as a new and distinct cultivar:

1. 5-petalled violet-colored flowers with a yellow throat measuring 1.5 cm in diameter;
2. Trailing vigorous growth;
3. Early flowering response; and
4. Suitable for use with hanging basket planters, combination planters and ground cover under full sunlight and slight shade.

Plants of 'Dancopink' differ from the plants of the female parent, 'CV-03-53' (unpatented) primarily in flower color and size. The flower size of 'Dancopink' is smaller than the parent, measuring 1.5 cm whereas the parent is 1.7 cm. The flower color of 'Dancopink' is darker violet than the parent. 'Dancopink' flowers are violet, RHS 84C, with RHS 84A to RHS 84B at the center, whereas 'CV-03-53' flowers are purple, RHS 76D, with 76A at the center.

Of the many commercial cultivars known to the inventor, the most similar in comparison to 'Dancopink' is the *Sutera* cultivar 'Copia Lavender' (unpatented). The new cultivar 'Dancopink' is distinguishable from 'Copia Lavender' in flower color. The flower color of 'Dancopink' is violet, RHS 84C, with violet, RHS 84A and RHS 84B, at the base of the petals, whereas 'Copia Lavender' flowers are violet-blue, RHS 91B.

BRIEF DESCRIPTION OF THE DRAWING

The accompanying photographic drawings illustrate the overall appearance of the new *Sutera* cultivar 'Dancopink' showing the colors as true as is reasonably possible with colored reproductions of this type. Colors in the photographs may differ slightly from the color value cited in the detailed botanical description which accurately describe the color of 'Dancopink'.

The first photograph shows a side view perspective of a typical 'Dancopink' plant in a hanging basket at 3 months.

The second photograph shows a close-up of the violet flowers of 'Dancopink' at 3 months.

DETAILED BOTANICAL DESCRIPTION

The new *Sutera* cultivar 'Dancopink' has not been observed under all possible environmental conditions. The phenotype of the new cultivar may vary significantly with variations in environment such as temperature, light intensity, and day length without any change in the genotype of the plant.

The aforementioned photographs, together with the following observations, measurements and values describe the new *Sutera* cultivar 'Dancopink' as grown in greenhouse in Moshav Mishmar Hashiva, Israel, under conditions which closely approximate those generally used in commercial practice.

Color references are made to The Royal Horticultural Society Colour Chart (R.H.S.), 2001, except where general colors of ordinary significance are used. Color values were taken under daylight conditions at approximately 12:00 pm. in Moshav Mishmar Hashiva, Israel. The age of the plant described is 3 months.

Classification:

*Botanical.*—*Sutera* sp.

Parentage:

*Female or seed parent.*—Proprietary cultivar designated 'CV-03-53' (unpatented).

*Male or pollen parent.*—Open pollination.

*Optimal growth conditions.*—

*Light intensities.*—Full sunlight, slight shade.

*Temperature.*—Day 20° C. to 24° C. Night 16° C. to 20° C.

*Temperature tolerance.*—Tolerant to low 5° C. to 7° C. and high 30° C. to 35° C. temperatures.

*Fertilization.*—A balanced fertilizer with level of 100 ppm Nitrogen.

*Growth regulators.*—Unnecessary.

Propagation: Tip cuttings of side shoots.

Plant:

*General appearance and form.*—Height: 7 cm. Spread: 42 cm. Shape: Trailing.

*Winter hardiness.*—Hardy in moderate climate.

*Vigor.*—Strong.

*Branching habit.*—Vigorously branched.

*Lateral branches.*—

TABLE 1

| Branch characteristic | Primary | Secondary |
|---|---|---|
| Length | 38 cm. | 14 cm. |
| Diameter | 2 mm. | 1 mm. |
| Internode Length | 2 cm. | 1.5 cm. |
| Texture | Slightly rough | Slightly rough |
| Pubescence | Present | Present |
| Color | Green, RHS 138B | Green, RHS 138B |

*Rooting habit and description.*—Easy to root. Time to initiate roots: 7 to 10 days. Time to produce a rooted cutting: 14 days.

*Crop time.*—8 to 10 weeks for a flowering pot.

*Fragrance.*—None.

Foliage:

*Overall shape of leaf.*—Rhomboidal.

*Base shape.*—Acute.

*Apex shape.*—Acute.

*Margin.*—Dentate.

*Texture.*—Slightly velvety.

*Pubescence.*—Slightly present.

*Leaf length.*—2.5 cm.

*Leaf width.*—1.7 cm.

*Color of upper surface.*—Mature leaf: Yellow-Green, RHS 147A. Immature leaf: Green, RHS 137A.

*Color of lower surface.*—Mature leaf: Green, RHS 137A. Immature leaf: Yellow-Green, RHS 146A.

*Venation color.*—Upper surface: Yellow-Green, RHS 147A. Lower surface: Green, RHS 137A.

*Petiole.*—Length: 5 mm. Diameter: 1 mm. Color: Yellow-Green, RHS 147A.

Flower description:

*Natural flowering season.*—All year round in moderate climate.

*Lastingness of the bloom.*—Flowering of a single flower lasts for 7 days.

*Quantity of flowers and buds per plant.*—Approximately 200.

*Flower size.*—Diameter (spread): 1.5 cm. Diameter at lobes: 15 mm. Diameter of corolla tube: 1 mm. Overall flower height: 8 mm.

*Flower bud.*—Height: 8 mm. Diameter: 4 mm. Color: Purple, RHS 76A. Shape: Spatulas.

*Petals.*—Shape: Oval. Length: 5 mm. Width: 5 mm. Apex: Rounded. Margin: Entire. Texture: Slightly velvety.

*Color.*—Upper surface, when opening: Violet, RHS 84B. Upper surface, opened flower: Violet, RHS 84C. Lower surface, when opening: Violet, RHS 84C. Lower surface, opened flower: Violet, RHS 84C.

*Corolla throat color.*—Yellow, RHS 13A.

*Calyx.*—Appearance: Deeply 5 lobed.

*Sepals.*—Shape: Linear. Length: 5 mm. Diameter: 2 mm. Quantity: 5. Apex: Acute. Margin: Entire. Upper surface color: Green, RHS 141A. Lower surface color: Green, RHS 141A.

*Pedicel.*—Aspect: Slanted upward. Length: 10 mm. Diameter: 1 mm. Angle: 45°. Color: Green, RHS 143A.

Reproductive organs:

*Stamen.*—Number: 4. Color: Yellow, 3A.

*Anthers.*—Color: Yellow, RHS 13A. Shape and length: Cylinder, 1 mm.

*Pollen.*—Color: Yellow, RHS 13A.

*Pistils.*—Quantity: 1. Length: 9 mm.

*Stigma.*—Shape: Undulate. Color: Yellow, RHS 3A.

*Ovary.*—Color: Green-Yellow, RHS 1C.

Seeds:

*Width.*—0.5 mm.

*Length.*—1 mm.

*Shape.*—Elliptic.

*Texture.*—Warty.

*Color.*—Greyed-Yellow, RHS 161C.

Fruit:

*Width.*—2 mm.

*Length.*—5 mm.

*Shape.*—Ellipsoid.

*Texture.*—Warty.

*Color.*—Greyed-Orange, RHS 165A.

Disease/pest resistance: No information is currently available.

Disease/pest susceptibility: No information is currently available.

I claim:

1. A new and distinct *Sutera* plant named 'Dancopink', substantially as illustrated and described herein.

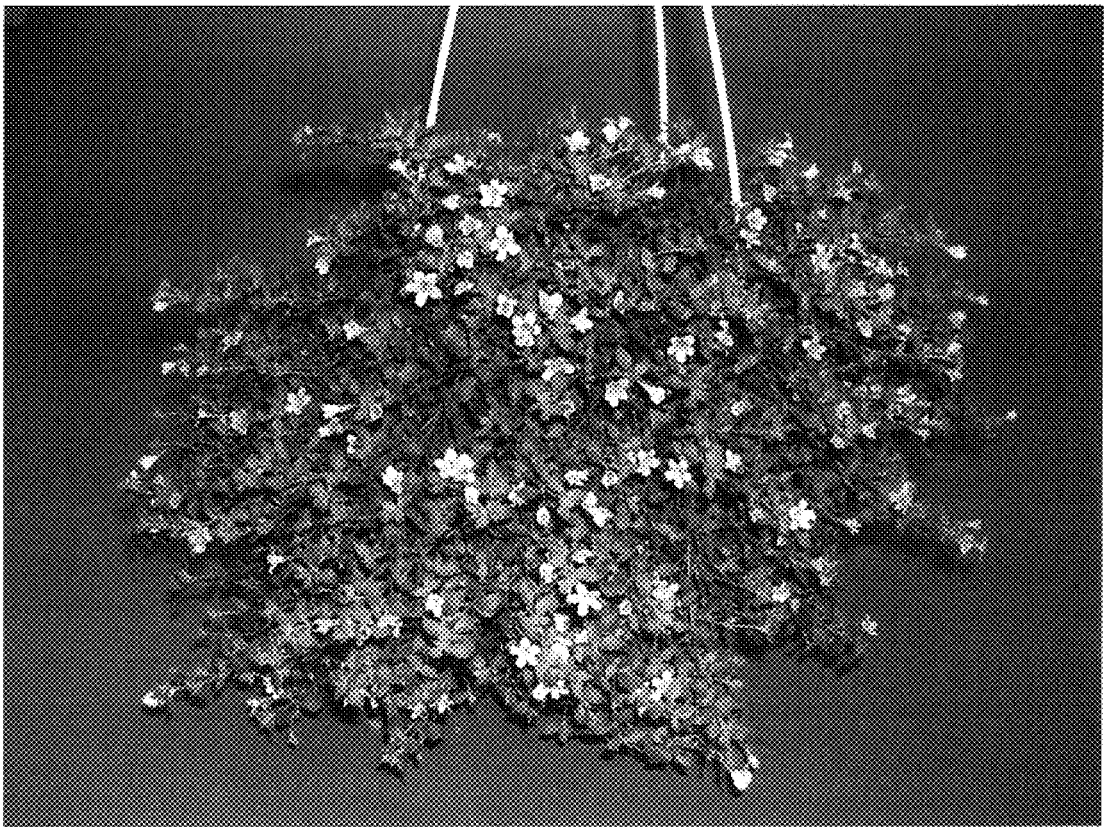

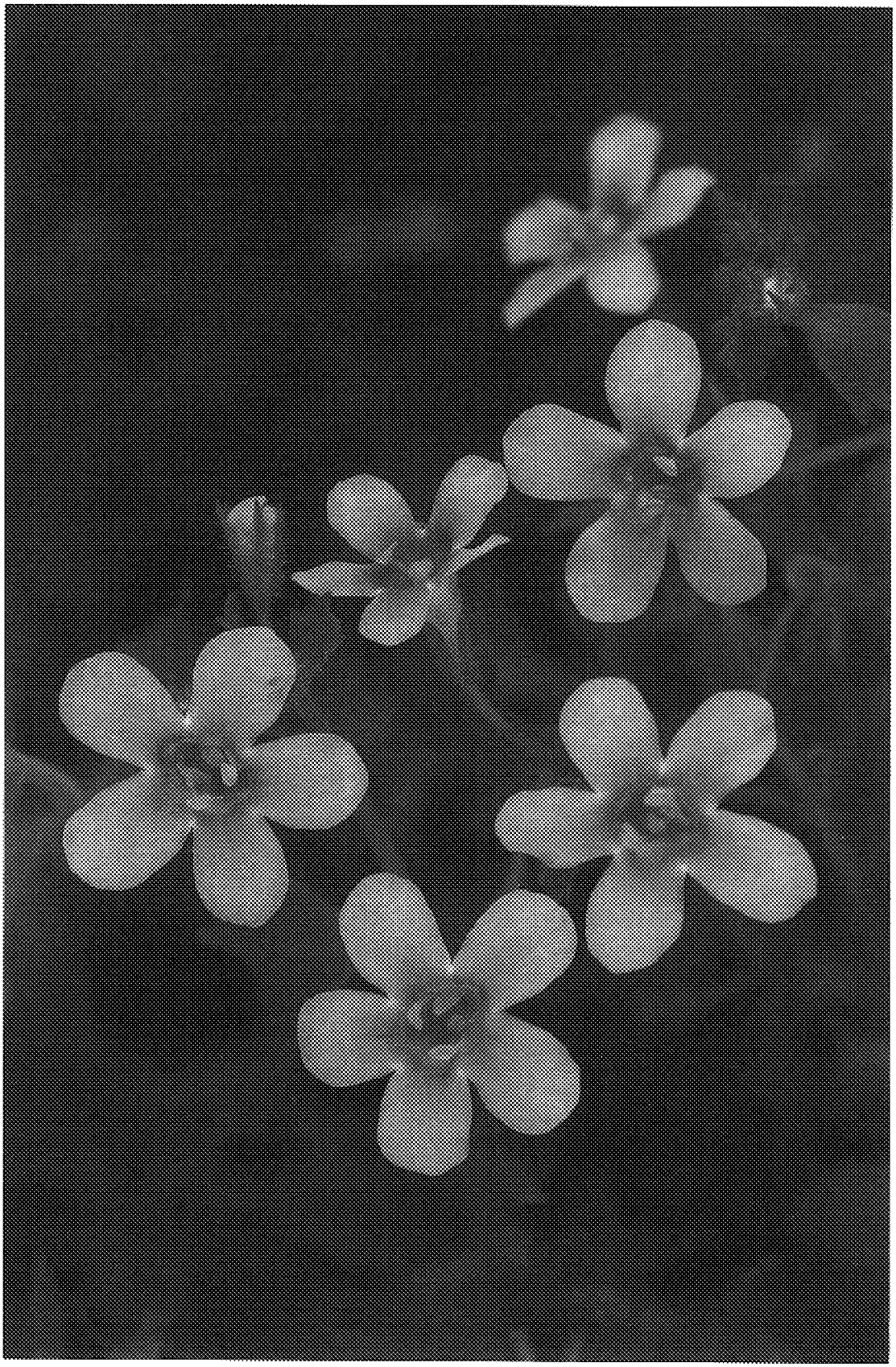

* * * * *